United States Patent
Barne et al.

(10) Patent No.: US 8,992,901 B2
(45) Date of Patent: *Mar. 31, 2015

(54) SKIN TREATMENT COMPOSITION

(75) Inventors: Sameer Keshav Barne, Bangalore (IN); Kalpana Kamalakar Nayak, Bangalore (IN); Aravindakshan Perincheery, Bangalore (IN); Maya Treesa Saji, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/698,679

(22) PCT Filed: May 17, 2011

(86) PCT No.: PCT/EP2011/057959
§ 371 (c)(1),
(2), (4) Date: Nov. 19, 2012

(87) PCT Pub. No.: WO2011/151172
PCT Pub. Date: Dec. 8, 2011

(65) Prior Publication Data
US 2013/0064785 A1    Mar. 14, 2013

(30) Foreign Application Priority Data

May 31, 2010    (IN) .................... 1653/MUM/2010

(51) Int. Cl.
| | | |
|---|---|---|
| *A61Q 17/00* | (2006.01) | |
| *A61K 47/32* | (2006.01) | |
| *A61K 8/81* | (2006.01) | |
| *A61K 8/86* | (2006.01) | |
| *A61K 8/31* | (2006.01) | |
| *A61K 8/34* | (2006.01) | |
| *A61K 8/35* | (2006.01) | |
| *A61K 8/37* | (2006.01) | |
| *A61K 8/49* | (2006.01) | |
| *A61Q 19/10* | (2006.01) | |

(52) U.S. Cl.
CPC ............ *A61K 8/8147* (2013.01); *A61K 8/31* (2013.01); *A61K 8/34* (2013.01); *A61K 8/342* (2013.01); *A61K 8/347* (2013.01); *A61K 8/35* (2013.01); *A61K 8/37* (2013.01); *A61K 8/498* (2013.01); *A61K 8/86* (2013.01); *A61Q 17/005* (2013.01); *A61Q 19/10* (2013.01)
USPC ...................... 424/78.07; 424/405

(58) Field of Classification Search
USPC ................... 424/78.07, 78.03, 405
See application file for complete search history.

(56) References Cited

U.S. PATENT DOCUMENTS

| | | | |
|---|---|---|---|
| 4,966,754 A | 10/1990 | Purohit et al. | |
| 5,939,050 A | 8/1999 | Iyer et al. | |
| 5,965,518 A | 10/1999 | Nakatsu et al. | |
| 6,210,695 B1 * | 4/2001 | Beerse et al. ................ | 424/404 |
| 6,248,705 B1 | 6/2001 | Cardola et al. | |
| 6,613,728 B1 | 9/2003 | Sirianni et al. | |
| 6,753,305 B2 | 6/2004 | Raso et al. | |
| 6,841,090 B1 | 1/2005 | Serego Allighieri et al. | |
| 6,921,745 B2 | 7/2005 | Yamada et al. | |
| 7,754,774 B2 | 7/2010 | Kobayashi et al. | |
| 2001/0000029 A1 | 3/2001 | Misumi | |
| 2002/0081270 A1 | 6/2002 | Delli Santi | |
| 2005/0019431 A1 | 1/2005 | Modak et al. | |
| 2007/0270321 A1 | 11/2007 | Barnhart et al. | |
| 2008/0044479 A1 | 2/2008 | Stack | |
| 2008/0051312 A1 * | 2/2008 | Lestage et al. ................ | 510/475 |
| 2008/0253976 A1 | 10/2008 | Scott et al. | |
| 2009/0035228 A1 | 2/2009 | Modak | |
| 2011/0223114 A1 | 9/2011 | Chakrabortty et al. | |
| 2012/0004641 A1 | 1/2012 | Bruehwiler et al. | |
| 2014/0170198 A1 | 6/2014 | Franklin et al. | |

FOREIGN PATENT DOCUMENTS

| | | |
|---|---|---|
| CH | 692411 | 6/2002 |
| CN | 1669576 | 9/2005 |
| CN | 101036459 | 9/2007 |
| CN | 101590287 A | 12/2009 |
| CN | 102229861 | 11/2011 |
| DE | 2263126 | 7/1973 |
| DE | 3117792 | 11/1982 |
| DE | 102004038285 | 4/2006 |
| EP | 0948892 A1 | 10/1999 |
| EP | 950399 | 10/1999 |
| EP | 0966883 A1 | 12/1999 |

(Continued)

OTHER PUBLICATIONS

PCT International Search Report in PCT application PCT/EP2011/057959 dated Feb. 24, 2012 with Written Opinion.
European Search Report in EP application EP 10 16 9778 dated May 12, 2011.
IPRP in PCTEP2012074399, Jul. 10, 2014, pp. 1-20, WO.
IPRP2 in PCTEP2012074409, Jul. 10, 2014.
IPRP2 in PCTEP2012074416, Jul. 10, 2014.
Biologically Active Substances of Plant Origin, Russian Academy of Sciences, 2001, RU.
Banayeva, A Study of The Chemical Composition of the Essential Oil of Representatives, Vegetable feed chemistry, 1999, 41-48, 3, RU.
Gablin, Balsamic fragrances Lemon thyme, Handmade Soaps, Jul. 18, 2007. 84. RU.

(Continued)

*Primary Examiner* — Ileana Popa
*Assistant Examiner* — Nicole Babson
(74) *Attorney, Agent, or Firm* — Ronald A. Koatz

(57) ABSTRACT

The invention is in the field of skin hygiene, especially hand hygiene and/or hand soap compositions. It remains to be desired to prepare skin hygiene compositions having a high anti-microbial effect, even with a low dosage of anti-microbial essential oils. It is therefore an object of the invention to provide a skin hygiene composition, having good anti-microbial properties, at low levels of essential oil. Surprisingly it has been found that composition comprising a low amount of at least two essential oils and a polymer provides improved hygiene efficacy.

4 Claims, No Drawings

(56) References Cited

FOREIGN PATENT DOCUMENTS

| | | |
|---|---|---|
| FR | 861920 | 2/1941 |
| FR | 1137 M | 2/1962 |
| FR | 2697133 | 4/1994 |
| FR | 2752730 | 3/1998 |
| FR | 2752730 A1 | 3/1998 |
| JP | 2012250937 | 12/2012 |
| KR | 100885511 | 2/2009 |
| KR | 20100123424 | 11/2010 |
| KR | 20120093607 | 8/2012 |
| SE | CH692411 | 6/2002 |
| WO | WO9713495 | 4/1997 |
| WO | WO9715277 | 5/1997 |
| WO | WO9801524 | 1/1998 |
| WO | WO0167868 A2 | 9/2001 |
| WO | WO0170215 A1 | 9/2001 |
| WO | WO03037270 A2 | 5/2003 |
| WO | WO2004006679 | 1/2004 |
| WO | WO2006012715 | 2/2006 |
| WO | WO2007125216 | 11/2007 |
| WO | WO2008035101 | 3/2008 |
| WO | WO2008085446 A2 | 7/2008 |
| WO | WO2008157847 | 12/2008 |
| WO | WO2009083521 A2 | 7/2009 |
| WO | WO2009085058 | 7/2009 |
| WO | WO2011036048 | 3/2011 |
| WO | WO2011151169 A1 | 12/2011 |
| WO | WO2011151171 A1 | 12/2011 |

OTHER PUBLICATIONS

Gablin, Balsamic fragrances Lemon thyme, Handmade Soaps, Jul. 18, 2007, 84, RU.
Umback et al., Georg Thieme Verlag, Kosmetik, 1995, 360-369, DE.
Zhigzhitzhapova, Chemical composition of an essential oil of Baikal thyme, Vegetable feed chemistry, 2008, 73-76, No. 1, RU.
Zhigzhitzhapova, The Chemical Composition of the Essential Oil of Baikal Thyme, Vegetable fee chemistry, 2008, 73-76, 1, RU.
Henkel Opposition against EP Patent No, 2 348 838 B1 dated Feb. 7, 2014.
Biersdorf Opposition against EP Patent No. 2 348 838 B1 dated Feb. 6, 2014.

* cited by examiner

SKIN TREATMENT COMPOSITION

FIELD OF THE INVENTION

The invention is in the field of skin hygiene, especially hand hygiene and/or hand soap compositions.

BACKGROUND OF THE INVENTION

Skin hygiene is of high priority to present day consumers. Consumers all over the world use various kinds of skin hygiene compositions.

Skin generally contains several different micro-organisms in concentrations exceeding millions or even billions of colony forming units (cfu's) per square centimeter ($cm^2$).

Many of these micro organisms are harmless, but there are also various pathogenic types or sub-species present, such as *Escherichia coli*, also referred to a *E. coli*, and *Staphylococcus aureus*, also referred to as *S. aureus*. Several other bacteria can be found in the skin flora, such as *Staphylococcus epidermidis*, also referred to as *S. epidermidis*, which is generally non-pathogenic, but is thought to be causing unpleasant body odour.

Therefore present day consumers appreciate skin care and cleansing products that have anti-microbial activity.

The most commonly known skin hygiene compositions predominantly consist of soap. Soap is a highly effective agent for killing bacteria. This is considered to be caused by its high alkalinity.

Various other skin hygiene materials have been proposed in the art. In recent years a number of publications have been made on the use of essential oils for anti-bacterial action.

In U.S. Pat. No. 5,965,518 essential oils are disclosed for use in fragrance compositions having antimicrobial activity.

In WO 01/70215, bactericidal composition comprising essential oils are disclosed for skin treatment and taught to reach even sub-dermal pathogens.

However, essential oils are relatively expensive ingredients. Additionally, essential oils are also known for their fragrances; using high amounts may cause a peculiar smell that is not always appreciated by the consumer.

Accordingly it remains to be desired to prepare skin hygiene compositions having a high anti-microbial effect, even with a low dosage of anti-microbial essential oils It is therefore an object of the invention to provide a skin hygiene composition, having good anti-microbial properties, at low levels of essential oil.

It is a further object of the invention to provide a composition that is effective against common skin and enteric bacteria, including both gram-positive and gram-negative bacteria.

Surprisingly it has been found that composition comprising a low amount of at least two essential oils and a polymer provides improved hygiene efficacy.

SUMMARY OF THE INVENTION

Accordingly the present invention provides in a first aspect, a skin treatment composition comprising a polymer A selected from the group of homopolymers and copolymers of carboxylic acid and derivatives or a polyalkylene oxide, and at least two essential oils selected from amyl salicylate, carvacrol, cymene, e.g. p-cymene, dihydroeugenol, eugenol, hexyl eugenol, hexyl salicylate, isoeugenol, methyl eugenol, methyl isoeugenol, methyl salicylate, tert butyl cresol, thymol, vanillin, cedrene, cineole, citral (including geranial and neral), citronellal, citronellol, eucalyptol (also known as 1,8 cineole) paradihydrolinalool, dihydromyrcenol (DH myrcenol), farnesol, geraniol, hexyl cinnamaldehyde, hydroxycitronallol, hydroxycitronellal, isocitral, limonene, preferably d-limonene, linalool, longifolene, menthol, nerol, nerolidiol, pinene, e.g. α-pinene, phellendrene, terpinene, e.g. α-terpinene and γ-terpinene, terpineol, e.g. γ-terpineol and terpin-4-ol, and tetrahydromyrcenol (THM).

In a second aspect the invention provides a method for providing an anti-microbial effect to skin comprising the steps of applying a composition according to the invention to the skin, and waiting for at least 15 seconds.

In a third aspect the invention provides the use of a composition comprising polymer A selected from the group of homopolymers and copolymers of carboxylic acid and derivatives or a polyalkylene oxide, and at least two essential oils selected from amyl salicylate, carvacrol, cymene, e.g. p-cymene, dihydroeugenol, eugenol, hexyl eugenol, hexyl salicylate, isoeugenol, methyl eugenol, methyl isoeugenol, methyl salicylate, tert butyl cresol, thymol, vanillin, cedrene, cineole, citral (including geranial and neral), citronellal, citronellol, eucalyptol (also known as 1,8 cineole) paradihydrolinalool, dihydromyrcenol (DH myrcenol), farnesol, geraniol, hexyl cinnamaldehyde, hydroxycitronallol, hydroxycitronellal, isocitral, limonene, preferably d-limonene, linalool, longifolene, menthol, nerol, nerolidiol, pinene, e.g. α-pinene, phellendrene, terpinene, e.g. α-terpinene and γ-terpinene, terpineol, e.g. γ-terpineol and terpin-4-ol, and tetrahydromyrcenol (THM), for providing an anti-microbial effect on skin.

By anti-microbial effect is meant being able to kill bacteria by at least 2 log (a factor 100) within 1 minute under standard test conditions (e.g. ASTM E2149-01) in-vitro.

By skin treatment composition is meant any composition for application onto skin. By skin is meant any keratinous substrate on the external surface of the body, including but not limited to, hands, face, underarm, hair and scalp.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The composition according to the invention thus comprises a polymer and at least two essential oils.

Polymer

According to the present invention, polymer A is a polymer selected from the group of homopolymers and copolymers of carboxylic acid and derivatives, or a polyalkylene oxide.

Polymer A, when being a homopolymer and/or copolymer of carboxylic acid and derivatives, has a plurality of carboxyl groups. The polymer A has a molecular mass preferably from 300 to $10^9$ D (Dalton, also referred to as atomic mass units, amu). The polymer A is selected from the class consisting of homopolymers or copolymers of carboxylic polymers, including natural synthetic and semi-synthetic polymers in this class.

The polymer may be a homo polymers or co polymers, wherein by copolymer of monomer X is meant any polymer that contains the monomer X and at least one further monomer.

Some non-limiting examples of polymer A according to the present invention include:

(a) homopolymers of a carboxylic acid, including but not limited to polycarboxylic acid such as polyacrylic acid, polymaleic acid or copolymers of acrylic and maleic acid.

(b) polysaccharides comprising carboxyl groups. Such polysaccharides may include (but are not limited to) starch, cellulose, sodium alginate, natural gums, and their modified materials such as sodium carboxymethyl cellulose, hydroxyethyl cellulose.

Alternatively the polymer A may be or a polyalkylene oxide, preferably poly ethylene oxide. Homopolymers or copolymers of poly alkylene oxide preferably have a molecular mass greater than $2 \times 10^4$ D. The molecular mass is preferably from $2 \times 10^4$ to $10^6$ D, more preferably from $3 \times 10^4$ to $5 \times 10^5$ D and most preferably from $5 \times 10^4$ to $2 \times 10^5$ D.

Homopolymers or copolymers of carboxylic acid have a molecular mass of preferably from $2 \times 10^3$ to $10^7$ D more preferably from $5 \times 10^4$ to $10^6$ D and most preferably from $9 \times 10^4$ to $5 \times 10^5$ D.

If the polymers are in particulate form, the particle size is preferably less than 200 µm, preferably less than 100 µm, more preferably less than 50 µm still more preferably less than 10 µm, or even less than 5 µm.

The homopolymers or copolymers of polysaccharide have a molecular mass of preferably from $10^3$ to $10^9$ D, more preferably from $10^4$ to $10^9$ D and most preferably from $10^5$ to $10^9$ D.

Polymer A is preferably at least partially neutralised in the Sodium ($Na^+$) form, preferably at least 10% w of polymer A is neutralised, more preferably at least 20%, still more preferably at least 50%.

Polymer A may be synthetic, semi-synthetic or natural. However, synthetic or semi-synthetic polymers are preferred.

Polymer A is preferably water soluble or water dispersible, most preferably polymer A is water soluble.

It is preferred that the polymer A is selected from a class consisting of homopolymers or copolymers of carboxylic acid.

The homopolymers or copolymers of carboxylic acid are preferably a polyacrylic acid or a copolymer thereof. Examples include SOKALAN® PA (BASF) and CARBOPOL® (Lubrizol).

The concentration of polymer A in the composition according to the invention is preferably between 0.001 and 25% by weight, more preferably at least 0.002%, or even at least 0.005%, but preferably not more than 15%, more preferably less than 5%, still more preferably less than 1%, even more preferably less than 0.5%, even less than 0.1%, or even less than 0.05% by weight of the composition.

Preferred polymers A are:

| Polymer A |
| --- |
| Polyacrylic acid (PAA) |
| Polyethylene Glycol (PEG) |
| Poly vinyl alcohol (PVA) |
| Sodium carboxymethyl cellulose (SCMC) |
| Hydroxyethyl cellulose |
| Starch-graft-polymethacrylic acid |
| Pluronic-g-Polyacrylic acid |
| Sodium carboxymethyl cellulose |

Optional Second Polymer B

In a preferred embodiment, the invention comprises the polymer A selected from the group of homopolymers and copolymers of carboxylic acid and derivatives, and a second polymer B selected from the group of homopolymers and copolymers of alkylene oxides, vinyl pyrrolidone and/or their derivatives; and/or the group of homopolymers and copolymers of vinyl alcohol, saccharides, hydroxyalkyl cellulose and/or their derivates;

Polymers A and B are preferably present in the composition in a ratio of between 1:5 and 5:1, more preferably between 1:2 and 2:1

Polymer B preferably has a monomeric unit comprising a group that can form hydrogen bonds with the carboxyl groups of polymer A.

Preferably, polymer B is selected from the group of homopolymers and copolymers of alkylene oxides, vinyl pyrrolidone and/or their derivatives; and/or the group of homopolymers and copolymers of vinyl alcohol, saccharides, hydroxyalkyl cellulose and/or their derivates.

The group of homopolymers and copolymers of vinyl alcohol, saccharides, hydroxyalkyl cellulose and/or their derivates, is generally not water soluble. In order to obtain the benefit of this group of polymers the particle size is set such that the particles are easily dispersible in water or and aqueous solution (i.e. a wash or rinse liquor). If the polymers are in particulate form, the particle size is preferably less than 200 µm, more preferably less than 100 µm, even more preferably less than 50 µm still more preferably less than 10 µm, or even less than 5 µm.

Polymers and homopolymers of carboxylic acid and/or sacchharides and/or polyalkylene glycol/ether qualify to be selected both as polymer A or polymer B, as they comprise hydroxyl or carboxyl group and either a carbonyl or an ether group. However, according to a preferred embodiment, polymer A and polymer B are not the same. It is particularly preferred that the polymers A and B are selected from different classes of polymers. Without wishing to be limited by theory, it is believed that the two polymers A and B, when dissolved in water, form a complex with a solubility lower than each of the polymers A and B, which helps in enhanced deposition and other benefits.

Polymer B preferably has a molecular mass from $10^3$ to $10^9$ D.

Homopolymers or copolymers of vinyl pyrrolidone or vinyl alcohol preferably have a molecular mass of between $10^3$ and $10^7$ D, more preferably from $10^4$ to $10^6$ D and most preferably from 30,000 to 500,000 D. Commercially available polyvinyl pyrrolidone can be used, one example of which is LUVISKOL® (BASF).

Homopolymers or copolymers of poly alkylene oxide preferably have a molecular mass greater than $2 \times 10^4$ D. The molecular mass is preferably from $2\times10^4$ to $10^6$ D, more preferably from $3\times10^4$ to $5\times10^5$ D and most preferably from $5\times10^4$ to $2\times10^5$ D.

Homopolymers or copolymers of saccharide preferably have a molecular mass of preferably from $10^3$ to $10^9$ D, more preferably from $10^4$ to $10^9$ D and most preferably from $10^5$ to $10^9$ D. Any commercially available poly alkylene oxide, for example POLYOX® (Dow Chemical Co) can be used according to the present invention.

Polymer B may be synthetic, semi-synthetic or natural. However, synthetic or semi-synthetic polymers are preferred.

According to a preferred embodiment, the polymer B is water soluble.

It is particularly preferred that the polymer B is selected from a class consisting of homopolymers or copolymers of vinyl pyrrolidone or alkylene oxide.

When present, the concentration of polymer B in the composition according to the invention is preferably between 0.001 and 20% by weight, more preferably at least 0.002%, or even at least 0.005%, but preferably not more than 10%, more preferably less than 5%, still more preferably less than 1%, even more preferably less than 0.5%, even less than 0.1%, or even less than 0.05% by weight of the composition.

Some examples of combinations of polymer A and polymer B, which are particularly preferred, are given below.

TABLE 1

Preferred combination of two polymers

| | |
|---|---|
| Polyacrylic acid (PAA) | Poly vinyl pyrrolidone (PVP) |
| Polyacrylic acid (PAA) | Polyethylene Oxide(PEO) |
| Polyacrylic acid (PAA) | Polyethylene Glycol (PEG) |
| Polyacrylic acid (PAA) | Poly vinyl alcohol (PVA) |
| Poly vinyl alcohol (PVA) | Polyethylene Oxide (PEO) |
| Sodium carboxymethyl cellulose (SCMC) | Polyethylene Oxide (PEO) |
| Hydroxyethyl cellulose | Polyacrylic acid(PAA) |
| Starch-graft-polymethacrylic acid | Polyethylene Oxide |
| Starch-graft-polymethacrylic acid | Polyvinyl pyrrolidone |
| Pluronic-g-Polyacrylic acid | Polyethylene Oxide |
| Pluronic-g-Polyacrylic acid | Polyvinyl pyrrolidone |
| Sodium carboxymethyl cellulose | Hydroxyethyl cellulose |
| Sodium carboxymethyl cellulose | Polyvinyl alcohol |

The most preferred combinations of the polymers are PAA-PVP, PAA-PEO, PEG-PAA, Starch-graft-polymethacrylic acid-Polyethylene Oxide.

Essential Oil

The compositions according to the inventions comprises at least two essential oils selected from aromatic essential oils including amyl salicylate, carvacrol, cymene, e.g. p-cymene, dihydroeugenol, eugenol, hexyl eugenol, hexyl salicylate, isoeugenol, methyl eugenol, methyl isoeugenol, methyl salicylate, tert butyl cresol, thymol, and vanillin; and non-aromatic essential oil terpenoid compounds including cedrene, cineole, citral (including geranial and neral), citronellal, citronellol, eucalyptol (also known as 1,8 cineole) paradihydrolinalool, dihydromyrcenol (DH myrcenol), farnesol, geraniol, hexyl cinnamaldehyde, hydroxycitronallol, hydroxycitronellal, isocitral, limonene, preferably d-limonene, linalool, longifolene, menthol, nerol, nerolidiol, pinene, e.g. α-pinene, phellendrene, terpinene, e.g. α-terpinene and γ-terpinene, terpineol, e.g. γ-terpineol and terpin-4-ol, and tetrahydromyrcenol (THM).

Although essential oils are often isolated from plants, they may also be obtained though synthetic or semi-synthetic routes.

The most preferred essential oils in the context of the present invention are thymol, terpineol and eugenol.

It is even more preferred that the composition comprises three essential oils, wherein the essential oils are still more preferably selected from a combination of a thymol, a terpineol and a eugenol.

Each essential oil is preferably present in the composition in a concentration of between 0.001 and 10% by weight of the composition, but preferably at least 0.002%, or even at least 0.005% by weight of the composition, while preferably not more than 5%, more preferably not more than 1%, still more preferably not more than 0.5%, or even not more than 0.1% by weight of the concentration.

Compositions

The compositions according to the invention may be applied in various skin care and cleansing products, including but not limited to hand soap, hand hygiene, deodorants, face wash, body wash and even shampoo and hair conditioner products. It is preferred that the compositions are applied to the skin neat, while the skin may be wet or dry at the time of application.

It is preferred that the contact time of the product with the skin before rinsing is at least 15 seconds, preferably at least 1 minute.

Stay on compositions, such as deodorants, skin hygiene compositions, skin care compositions may stay for a longer period of time, preferably at least 15 seconds, more preferably 1 minute, even more preferably at least 15 minutes, still more preferably at least 1 hour, still more preferably at least 2 hours, or even more than 5 hours.

The pH of the compositions is preferably neutral or mildly acidic, more preferably between pH 2 and 9, still more preferably at least pH 3, while more preferably less than pH 8, still more preferably less than pH 7, or even less than pH 6.

Method

Consequently there is provided a method for providing an anti-microbial effect to skin comprising the steps of applying a composition according to the invention to the skin, and waiting for at least 15 seconds.

For hand/skin hygiene applications, skin care applications and deodorant applications the composition is preferably left on the skin after application without rinsing, but may be wiped of after the indicated time.

For hand soap, face and body wash and shampoo and hair conditioner applications, the skin is preferably rinsed after application and after the indicated time.

EXAMPLES

The invention will now be illustrated by means of the following non-limiting examples.

Example 1

Anti-Microbial Efficacy Test (In Vitro) Against *E. coli* at pH 3.5

The protocol used for testing in-vitro is based on standard test method ASTM E2149-01, wherein working cultures of individual bacterial species (*E. coli* ATCC 10536 as indicated below) were added to the test samples; and were given a 15 seconds contact time. The samples were neutralized and serially diluted in a neutralizer. The viable count is determined by agar pour plating. Activity is assessed by comparing the size of the population of untreated with that of treated specimens.

Test compositions and bacterial kill results are given in the table below:

| | Blank (% w) | Comp A (% w) | Comp B (% w) | Ex 1 (% w) |
|---|---|---|---|---|
| *E. coli* (start, cfu/ml) | $24.25 \times 10^6$ | $24.25 \times 10^6$ | $24.25 \times 10^6$ | $24.25 \times 10^6$ |
| PAA[1] | | 0.015 | | 0.015 |
| Thymol | | | 0.025 | 0.025 |

-continued

|  | Blank (% w) | Comp A (% w) | Comp B (% w) | Ex 1 (% w) |
|---|---|---|---|---|
| Terpineol |  |  | 0.062 | 0.062 |
| Saline solution[2] | balance | Balance | Balance | Balance |
| Kill (cfu/ml remaining) | $24.25 \times 10^6$ | $15.5 \times 10^6$ | $5.4 \times 10^6$ | 0 |
| Kill (log reduction) | 0.0 | 0.2 | 0.7 | 7.4 |

[1] The polymer is PAA (poly acrylic acid; Mw 100,000 D, ex Sigma-Aldrich)
[2] The saline solution comprised 0.1% NaCl and Citric acid to a pH of 3.

The table above shows that the composition of polymer and two essential oils provides the objected effect at 15 seconds contact time.

Example 2

Anti-Microbial Efficacy Test (In Vitro) Against *E. coli*—at Different pH

The same method was used as in example 1, but a contact time of only 15 seconds was used in this example.

Test compositions and bacterial kill results are given in the table below:

|  | Blank (% w) | Comp C (% w) | Comp D (% w) | Ex 2 (% w) | Ex 3 (% w) | Ex 4 (% w) | Ex 5 (% w) |
|---|---|---|---|---|---|---|---|
| *E. coli* (start, cfu/ml) | $15 \times 10^6$ | $15 \times 10^6$ | $15 \times 10^6$ | $15 \times 10^6$ | $15 \times 10^6$ | $15 \times 10^6$ | $15 \times 10^6$ |
| pH | 3.5 | 3.5 | 3.5 | 3.5 | 6 | 8 | 6 |
| PAA[1] |  | 0.015 |  | 0.015 | 0.015 | 0.015 | 0.03 |
| Thymol |  |  | 0.025 | 0.025 | 0.025 | 0.025 | 0.025 |
| Terpineol |  |  | 0.062 | 0.062 | 0.062 | 0.062 | 0.062 |
| Saline solution[2] | balance | balance | Balance | balance | Balance | Balance | Balance |
| Kill (cfu/ml remaining) | $15 \times 10^6$ | $14.3 \times 10^6$ | $6.3 \times 10^6$ | 0 | 257 | 2700 | 90 |
| Kill (log reduction) | 0.0 | 0.1 | 0.4 | 7.2 | 6.1 | 3.8 | 6.3 |

[1] The polymer was PAA (poly acrylic acid; Mw 100,000 D, ex Sigma-Aldrich)
[2] The saline solution comprised 0.1% NaCl and Citric acid to the indicated pH.

The table above demonstrates that good results are obtained at different pH's.

Example 3

Comparative Tests: Anti-Microbial Efficacy Test (In Vitro) Against *E. coli*—Effect of Single Polymers The test method as given above was used.

Test compositions and bacterial kill results are given in the table below:

|  | Blank (% w) | Ex 6 (% w) | Ex 7 (% w) |
|---|---|---|---|
| *E. coli* (start, cfu/ml) | $24.25 \times 10^6$ | $24.25 \times 10^6$ | $24.25 \times 10^6$ |
| PAA[1] |  | 0.015 |  |

-continued

|  | Blank (% w) | Ex 6 (% w) | Ex 7 (% w) |
|---|---|---|---|
| PEO[1] |  |  | 0.01 |
| Thymol |  | 0.025 | 0.025 |
| Terpineol |  | 0.062 | 0.062 |
| Saline solution[2] | balance | Balance | balance |
| Kill (cfu/ml remaining) | $24.25 \times 10^6$ | 0 | $0.44 \times 10^6$ |
| Kill (log reduction) | 0.0 | 7.4 | 2.2 |

[1] The polymer complex comprised PAA (poly acrylic acid; Mw 450,100,000 D, ex Sigma-Aldrich) and PEO (poly ethylene oxide; Mw 100,000 D, ex Sigma-Aldrich), in an amount as given in the table.
[2] The saline solution comprised 0.1% NaCl and Citric acid to a pH of 3.6.

The table above shows that the single polymers do provide the objected effect at 15 seconds contact time.

Example 4

A Typical Hand Sanitizer According the Invention

A typical hand sanitizer composition according to the invention is given in the table below.

| Ingredients | Example composition 8 % wt/wt |
|---|---|
| Carbopol ETD 2020 (poly acrylic acid) | 0.015 |
| Phenoxy ethanol | 0.2 |
| Disodium EDTA | 0.05 |
| Methyl paraben | 0.2 |
| Terpineol | 0.05 |
| Thymol | 0.025 |
| Eugenol | 0.005 |
| DM water | Rest |
| Total | 100 |

The composition given above provides long lasting hygiene when applied to skin.

Example 5

Hand Soap Composition

| Ingredients | Example composition 9 % wt/wt | Example composition 10 % wt/wt |
|---|---|---|
| SODIUM LAURETH SULFATE 1EO 70% | 10 | 10 |
| Cocoamidopropyl betaine | 10 | 10 |
| GLYCERIN | 2 | 2 |
| ISOPROPYL PALMITATE | 0.25 | 0.25 |
| Carbopol ETD 2020 (Poly acrylic acid) | 0.03 | |
| Poly ethylene oxide | | 0.02 |
| Citric acid mono hydrate | 0.50 | 0.50 |
| Terpineol | 0.05 | 0.05 |
| Eugenol | 0.01 | 0.01 |
| Thymol | 0.03 | 0.03 |
| Water | rest | Rest |
| Total | 100 | 100 |

The compositions given above provide anti bacterial effect on skin within 15 seconds.

The invention claimed is:

1. A method of providing an anti-microbial effect to skin comprising the steps of
    (i) applying a composition to the skin comprising
        (a) a polymer A selected from the group consisting of polyacrylic acid and poly ethylene oxide, said poly ethylene oxide having a molecular mass greater than $2 \times 10^4$ D, and
        (b) at least two essential oils selected from eugenol, thymol and terpineol, wherein a mixture of thymol and terpineol is required, and
    (ii) waiting for at least 15 seconds before rinsing the product from the skin.

2. A method according to claim 1, wherein polymer A is present in a concentration of between 0.001 and 25% by weight of the composition.

3. A method according to claim 2, wherein the essential oil is present in a concentration of between 0.001 and 0.5% by weight of the composition.

4. A method according to claim 1, wherein the pH of the composition is between 2 and 9.

* * * * *